(12) United States Patent
Maksyutenko et al.

(10) Patent No.: US 9,234,837 B2
(45) Date of Patent: Jan. 12, 2016

(54) OPTICAL GAS ANALYZER

(71) Applicants: Michail A. Maksyutenko, St. Petersburg (RU); Sergey V. Nepomnyashchy, St. Petersburg (RU); Sofia B. Pogodina, St. Petersburg (RU); Vyacheslav V. Khrebtov, St. Petersburg (RU)

(72) Inventors: Michail A. Maksyutenko, St. Petersburg (RU); Sergey V. Nepomnyashchy, St. Petersburg (RU); Sofia B. Pogodina, St. Petersburg (RU); Vyacheslav V. Khrebtov, St. Petersburg (RU)

( * ) Notice: Subject to any disclaimer, the term of this patent is extended or adjusted under 35 U.S.C. 154(b) by 0 days.

(21) Appl. No.: 14/690,683

(22) Filed: Apr. 20, 2015

(65) Prior Publication Data

US 2015/0241339 A1    Aug. 27, 2015

Related U.S. Application Data

(63) Continuation-in-part of application No. 13/885,097, filed as application No. PCT/RU2011/000894 on Nov. 11, 2011, now abandoned.

(51) Int. Cl.
*G01J 5/02* (2006.01)
*G01N 21/3504* (2014.01)
*G01N 21/03* (2006.01)

(52) U.S. Cl.
CPC .......... *G01N 21/3504* (2013.01); *G01N 21/031* (2013.01)

(58) Field of Classification Search
CPC ...................................... G01N 21/35

USPC ........... 250/343, 338.1, 339.13; 356/436–438
See application file for complete search history.

(56) References Cited

U.S. PATENT DOCUMENTS 3,860,818 A * 1/1975 Stalder et al. ................. 250/343
5,957,858 A * 9/1999 Micheels et al. .............. 600/529

OTHER PUBLICATIONS

Johnston, S. E., "Gas monitors employing infrared LEDs", Meas. Sci. Technol. 3, Feb. 1992, pp. 191-195.*

* cited by examiner

*Primary Examiner* — David Porta
*Assistant Examiner* — Meenakshi Sahu
(74) *Attorney, Agent, or Firm* — Alexander Rabinovich

(57) ABSTRACT

An optical gas analyzer, preferably for hydrocarbons, comprises an optical gas cell, an infrared LED pulse radiation source and a radiation detector at the inlet and outlet of the cell, respectively, and a control unit. The detector comprises measuring and reference photovoltaic detectors, a filter window at the detector inlet, and a filter mirror inside the same. Resulting spectral transmission and reflection characteristics of the filter window and filter mirror match the absorption spectrum for the gas and the radiation spectrum of the source. The filter window and filter mirror compensate external influence upon the radiation path trajectory within the cell on the gas concentration result. The cell comprises spherical or parabolic and flat mirrors arranged in a checker order to transmit the beam of the source via a zigzag-like trajectory between the mirrors. The analyzer offers a fast response and high sensitivity along with minimized power consumption and dimensions.

8 Claims, 7 Drawing Sheets

OPTICAL GAS ANALYZER

CROSS-REFERENCE TO RELATED APPLICATIONS

This application is a continuation-in-part of U.S. application Ser. No. 13/885,097 filed May 13, 2013, which is a National phase application of PCT/RU2011/000894 filed Nov. 11, 2011, claiming priority to Russian application RU2010147341 filed Nov. 12, 2010, all three applications being hereby incorporated by reference in their entirety.

TECHNICAL FIELD

The following description generally relates to the field of measurement technique, and more specifically to devices for controlling the content of hydrocarbons in the atmosphere. These devices represent measuring apparatuses, mostly portable, configured to continuously control the level of explosive concentrations of, for example, methane within industrial premises or mines, by means of measuring and analyzing the gas, incoming into the device from environment, via molecular diffusion, i.e. without creating a positive gas flow.

TECHNICAL BACKGROUND

Known has been an infrared absorption gas analyzer (patent RU 2292039, IPC G01N21/61, publ. 2005-02-18), hereinafter referred to as a gas analyzer, that comprises a control unit, an optical gas cell, an infrared radiation (hereinafter referred to as IR) source and an IR detector. The IR radiation source is installed at the cell inlet, while the IR radiation detector is installed at the cell outlet. The control unit is adapted to process the IR radiation, received by the detector, to display the results of the processing. Also, the IR radiation source has a spherical mirror reflector. The optical gas cell includes operational and reference chambers, wherein the operational chamber is shaped like a hollow frustum of a cone with an internal spherical mirror reflector and is installed immediately within the reference chamber in the optical axis with the IR radiation source, whereas the IR radiation detector comprises a focusing unit and is installed along an optical axis perpendicular to the first one. A mirror splitter and a rotating disc with a profile window are placed at the cross point of these axes.

This gas analyzer has such significant disadvantages as:
high energy consumption due to the loss of a substantial energy portion of the IR radiation source at the mirror reflector and due to the IR radiation flow interruption by the disc with a profile window, because only small areas within the wide spectrum of the IR radiation of the source are used;
reduced operational reliability due to having a multitude of mechanical parts, such as, for example, the rotating disc with the profile window and a rotating optical filter; and
increased overall dimensions resulting mainly from a large number of space consuming mechanical parts, and spherical mirror reflectors, with their mutual allocation.

A gas analyzer is known (EPA 2169384, IPC G01N21/35, publ. 2010-03-31) intended for the creation of a multi-component apparatus, to be used within stationary facilities or at mobile medical stations for monitoring human breath gases with sufficient accuracy provided by means of compensating the external influences upon the radiation path trajectory. Herein, this task is solved through the use of an infrared radiation source, a gas cell, a dichroic beam splitter, an analyzing filter, a reference detector, and a measuring detector. In this case, the dichroic beam splitter is adapted to change the beam angle depending on the gas analyzed. The dichroic beam splitter is installed at 45° to the normals of the photodetectors located at 90° to each other.

The disadvantages of this analyzer include large dimensions and high energy consumption.

Known from Russian patent 2372606, IPC G01N21/03, publ. 2009-11-10, is a miniature multi-path mirrored optical cell. The cell fails to protect against temperature external conditions.

Known has been an infrared gas analyzer (U.S. Pat. No. 6,114,700, IPC G01N21/05, publ. Sep. 5, 2000), wherein photovoltaic detectors are used as infrared radiation detectors. However, the use of the photovoltaic detector in the known gas analyzer does not provide a balance of high detectability and fast response.

Also known has been an optical gas sensor device based on the immersion diode optical pairs is known (RU 75885, IPC G01N21/35, publ. Aug. 27, 2008), comprising a gas cell, the reflecting surfaces of which form an optical scheme for generating a probe radiation beam, as well as a probe IR radiation source including a light-emitting diode (LED) and a photodetector including a photodiode, which are mechanically connected to the gas cell body. The gas cell comprises mechanical adjusting elements, the light-emitting diode and photodiode being implemented with the use of immersion optics (immersion diodes) and rigidly connected to the adjusting elements.

The disadvantage of the known device is the use of the immersion diodes, which possess uncontrollable axis misalignment of optical scheme and diagrams. The use of immersion diodes results in the complication of the gas analyzer design due to having to add adjusting devices, and in the increase in dimensions.

Known also has been an infrared band gas analyzer (RU 2287803, IPC G01N21/35, publ. Nov. 20, 2006), comprising a wave power source including a light-emitting diode matrix, emitting a reference and operating wave lengths, a gas cell located along the radiation, a main photodetector installed at the cell outlet to receive the reference and operating wave length radiation, as well as a signal processing unit, comprising analog-to-digital coder (ADC), with its outlet connected to a microprocessor and an indication unit. An additional photodetector is installed at the cell inlet, the both photodetectors including pyroelectric photodetectors.

Each light-emitting diode within the light-emitting diode matrix of this known gas analyzer should have fast response when powered by pulse current, to keep the total power unvarying.

When using such matrix, however, it is impossible to facilitate a simultaneous beaming concentration on a single photodetector for each light-emitting diode within the matrix and, at the same time, to minimize optical unit dimensions. Also, the infrared sources are used in the prior art in conjunction with photodetectors of pyroelectric type.

An optical gas sensor, hereinafter referred to as a gas analyzer and known from EP 1995586, IPC G01N21/03, publ. Nov. 26, 2008, comprises a radiation source, an optical gas cell, and an optical radiation detector. Through the optical gas cell, from the inlet to the outlet thereof, two curved channels are formed for passing IR radiation which is emitted from the source located at the inlet of the optical gas cell and is directed towards the detector installed at the outlet of the above-mentioned cell, the channels being spatially separated, their curve radii fitting the body of the optical gas cell. There is a control unit coupled with the radiation source and the optical radiation detector and adapted to change operation modes of the IR radiation source and to process the IR radiation received by the detector displaying the results obtained therefrom.

This gas analyzer possesses such disadvantages as:

substantial losses of the energy of the IR radiation due to having two curved channels for passing same, as well as due to the necessity of the radiation transfer from one channel to another; and delayed action in operation resulting from slow gas delivery into the channels due to the gas having to self-diffuse inwards the two channels.

Also known has been a gas monitor comprising IR light-emitting diodes (S. F. Johnston: Gas monitors employing infrared LEDs, *Meas. Sci. Technol.* 3 (1992) 191-195). A compact version of the monitor provides for registering concentrations of carbon dioxide ($CO_2$). It cannot be used, however, for monitoring methane ($CH_4$) concentrations because, since the absorption factor of $CO_2$ is ten times that of $CH_4$, the monitor for $CO_2$ requires one tenth of optical path length as compared with that for $CH_4$. The impossibility of making a compact version of a hydrocarbon concentration monitor using the design disclosed in Johnston is believed to be a serious drawback of that prior art.

An integrated optical gas sensor known from the GB patent 2401432, IPC G01N21/03, publ. Nov. 10, 2004 and hereinafter referred to as an optical gas analyzer comprises an optical gas cell, an IR radiation source and a detector of this radiation. The optical gas cell is configured to pass IR radiation from its source to the detector of this radiation and is implemented curve-shaped with a rectangular cross-section. A electric bulb is used as a source of IR radiation and is located at the inlet of the cell, and the IR radiation detector is located at the outlet of the cell. There is a control unit coupled with the radiation source and the optical radiation detector and adapted to change operation modes of the IR radiation source and to process the IR radiation received by the detector displaying the results obtained therefrom.

This prior art is selected as the closest analog of the claimed gas analyzer since they have the greatest number of common essential features common with the claimed gas analyzer and are intended to solve similar tasks.

The prior art has such disadvantages as:

substantial infrared radiation energy losses resulting from the curve-shaped implementation of the cell wherein, due to the specificity of the IR radiation reflection from the curved surface of the gas cell internal walls, there is strong dissipation of the radiation energy;

large energy consumption since an electric bulb is used as an IR radiation source, and a pyroelectric detector is used as an IR radiation detector, which results in a control unit to function at low frequencies with lower duty ratio;

a low level of the IR radiation energy registered by the detector due to a large angle of radiation divergence when it leaves the cell and when it reaches the detector, as well as due to the strong IR radiation energy dissipation resulting from the cell curved shape.

Besides, the optical gas cell developed within this design is not capable to concentrate the IR radiation on the detector plane, since it is implemented as a light guide with reflection from its walls.

SUMMARY OF THE PROPOSITION

The object of the technical solution proposed in the present disclosure is to provide an optical gas analyzer configured to achieve a high IR radiation transmission coefficient, as well as a higher sensitivity with minimum energy consumption and small dimensions.

The above objective is met by providing an optical gas analyzer that comprises an optical gas cell for the infrared radiation to pass through, an infrared radiation source located at the inlet of the optical gas cell, and also an infrared radiation detector located at the outlet of the above-mentioned cell, a control unit connected to the infrared radiation source and the infrared radiation detector, the control unit being adapted to change operation modes of the infrared radiation source, and to process the infrared radiation, received by the detector, to display the results obtained. According to the disclosure, the optical gas cell is a multi-path and mirror one, adapted to concentrate the infrared radiation passing therethrough, from the inlet thereof, in areas on a way through it, and at the outlet from it at the infrared radiation detector. The infrared radiation detector includes a differential receiving device comprising a measuring photovoltaic detector and a reference photovoltaic detector, the receiving device additionally comprising a filter window located at its inlet, and a filter mirror adapted by its location to compensate external influence upon the infrared radiation path trajectory within the above-mentioned cell on the gas concentration result to be measured, whereas their resulting spectral transmission and reflection characteristics correlate with the absorption spectrum for the gas to be measured and with the radiation spectrum of the infrared radiation source, respectively, the infrared radiation source including the infrared impulse source of the LED type creating a directed infrared radiation at the inlet of the optical gas cell, with the source switching on/off duty rate being correlated by the control unit with the same for the receiving device.

Thanks to the aggregation of essential features/limitations, this new technical solution provides for creation a new optical gas analyzer, which facilitates the following technical results: achieving maximum sensitivity due to the source radiation energy concentration and due to the compensation of the external influence on the infrared radiation path trajectory through the long optical path within the above-mentioned cell; and providing for minimum energy consumption due to the usage of the proper impulse infrared radiation source and IR radiation detector, whose on/off duty rates are correlated by the control unit, and due to reducing the radiation energy dissipation.

Compared to the gas analyzer from the closest analog, the present optical gas analyzer has essential differences. There is a filter window located at the inlet of the receiving device and forming—in conjunction with the filter mirror located within the receiving device—a stable spectral characteristic, namely, an apparatus spectrum function, that makes it possible to compensate external influences, exerted upon the infrared radiation path trajectory through the cell, on the gas concentration result to be measured. Additionally, the resulting spectral transmission and reflection characteristics of the filter window and the filter mirror correlate with the absorption spectrum for the gas to be measured, and with the radiation spectrum of the infrared radiation source, respectively. Also, the control unit correlates the switching on/off duty rate of the infrared radiation source with the switching on/off duty rate of the differential photovoltaic detector, receiving this radiation. Thus, the suggested gas analyzer has essential differences.

The subject matter comprises a solution for the task of creating a new portable gas analyzer, to be used particularly for personal safety while being under extreme conditions, to provide for the following technical result: achieving maximum sensitivity with simultaneous minimum energy consumption and small overall dimensions. Attaining these results is a controversial task. For example, to bring about maximum sensitivity, one has to secure maximum optical length for the radiation distribution path, that implies an increase of the device design dimensions. The minimum energy consumption contradicts achieving the maximum sensitivity for one has to provide passing as much radiation as possible through a long optical path within the cell. The gas analyzer represented herein facilitates solution of the above-mentioned conflict.

The gas analyzer of the subject matter provides for the compensation of mechanical influences upon the radiation passage trajectory to be carried out in at least two stages. During the first stage, the compensation results from the designed mutual location of the spherical elements within the cell, since the spherical elements are located in such a way as to compensate the beam deviation that appears because of the mechanical influence imposed upon the cell body. At the second stage, the mechanical compensation takes place at the cell outlet owing to the use of a differential detector that incorporates, both operationally and by design, two photo-sensible sites, a filter window and a filter mirror. The present analyzer provides for the in-phase shift, i.e. if the beam at the cell outlet is shifted, then it is shifted at both photo-sensible sites in the same direction and for the same distance. As this takes place, as shown experimentally, it becomes possible to compensate the beam trajectory deviation resulting from the external mechanical influence for the angle of about 10°.

Thus, it is believed that the present analyzer is more advanced in implementing the principle of mechanical compensation, because, as known, the less is the distance between the splitter center and the photo-sensible site, the more is the drop angle of radiation beam that can be compensated by virtue of the system described. In addition, the compensation takes place in two stages, thus providing further compensation quality improvement at the second stage.

In this disclosure, the source of the infrared radiation includes a LED-type source with a specific narrow radiation spectrum, approximately 80% of the energy from the source being employed. This comes about since after the radiation has passed through the cell with the gas to be analyzed, the radiation spectrum ends up in the filter window, and then in the filter mirror adapted to reflect about 51-52% of the source energy towards the reference detector, whereas the measuring detector acquires a portion of the radiation spectrum (within 22-23% of the source energy) passing through the filter mirror and containing the area of wave lengths absorbed by the gas to be analyzed. Thus, the gas analyzer presented herein carries out coordination of the spectral transmission and reflection characteristics with the spectrum of absorption of the gas to be analyzed and radiation spectrum of the infrared source, respectively. This contributes to lowering energy consumption, the overall LED type source energy efficiency amounting to 74-75% of the source energy.

In the present analyzer, the measuring and the reference detectors are operationally and structurally combined within a single receiving device, the filter mirror aggregating the beam splitter and the analyzing filter. An optical scheme of the present gas analyzer provides a multifold increase in efficiency of the infrared emitter energy usage, both from viewpoint of the use of the source radiation spectral band, and from viewpoint of the source beam energy concentration on each of the photo-receiving sites. This is critically important for the task to be solved: designing a micro-consuming gas analyzer.

Thus, the gas analyzer being described herein achieves a high infrared radiation energy transfer coefficient in conjunction with maximum infrared radiation energy efficiency and with small dimensions.

Small overall dimensions of the apparatus being described herein result from functional and design aggregation of the photosensitive elements, the filter mirror, and the filter window within a single photo-receiving device, and also from using the optical gas cell adapted to concentrate this radiation as it passes areas within the cell and exits the same towards the infrared radiation detector, thus facilitating maximum sensitivity. In this way, a longer optical path is created with smaller cell dimensions.

The optical gas cell is adapted to concentrate the radiation, from the inlet thereof, in areas on a way through it, and at the outlet from it, at the infrared radiation detector. At this, the infrared radiation detector represents a differential receiving device that includes a measuring photovoltaic detector, and a reference photovoltaic detector, which in turn are fast photovoltaic elements, whereas the infrared radiation source includes a pulse source, the source on/off duty rate matching, via the control unit, the same of the differential detector.

The main advantage of the analyzer when using a photovoltaic detector is a combination of high detectability with fast response. To reduce energy consumption, the infrared radiation source selected operates in a mode of short powerful pulses thus requiring a fast detector capable to catch these pulses. Moreover, the source on/off duty rate matches, via the control unit, the same of the differential detector.

In an embodiment of the optical gas analyzer, the optical gas cell, that facilitates concentration of the infrared radiation passing therethrough, is formed of flat mirrors and spherical or parabolic mirrors, the number of the latters exceeding the number of flat ones. In this case, the infrared radiation source is directed towards the first spherical mirror which is placed at the corresponding angle to the main optical axis of the gas cell. The latter is adapted to transmit the radiation energy by the zigzag-like trajectory with multiple radiation concentration between the mirrors. Thus, an image of the source is created upon the flat mirrors and on the receiving device, where the filter mirror is installed at an angle of 45 degrees to normal lines of the measuring and the reference photovoltaic detectors located at 90° to each other. According to the subject matter, the efficient use of the multi-path mirrored optical cell is possible if a pulse light-emitting diode is used as the infrared radiation source. In this case, the differential receiving device is located so that the radiation source image plane at the outlet of the cell coincides with the plane of the measuring photovoltaic detector location, the design of the receiving device automatically providing for the correspondence of the radiation source image plane and the plane of the second (reference photovoltaic detector) location. This facilitates achieving the claimed technical result, namely, measurement sensitivity increase due to the radiation energy concentration.

The present optical gas cell in conjunction with the suggested structural elements, can be used most effectively, facilitating not only compensation of external mechanical influences on measurements, but also minimizing the overall device dimensions, as discussed above.

The usage of semiconductor elements in the present gas analyzer as a detector and radiation source having properties of fast response and low energy consumption is necessary, but not sufficient to achieve fast response with simultaneous energy consumption minimization and small dimensions of the device. It is, for example, only with corresponding power supply modes that the infrared pulse light-emitting diodes known for their fast response provide also for the low energy consumption, the operation of the control unit of the analyzer playing a significant part therein.

It is the plurality of essential features that facilitates achieving higher transmission coefficient of the infrared radiation with the maximum usage of the infrared radiation energy and small dimensions, and with providing for the infrared radiation to pass from the cell inlet to the outlet thereof towards the detector of the radiation along the large optical path.

BRIEF DESCRIPTION OF THE DRAWINGS

The optical gas analyzer according to the present disclosure will be better understood from the ensuing description with the accompanying drawings where.

DETAILED DESCRIPTION OF THE ANALYZER

Figure 1:
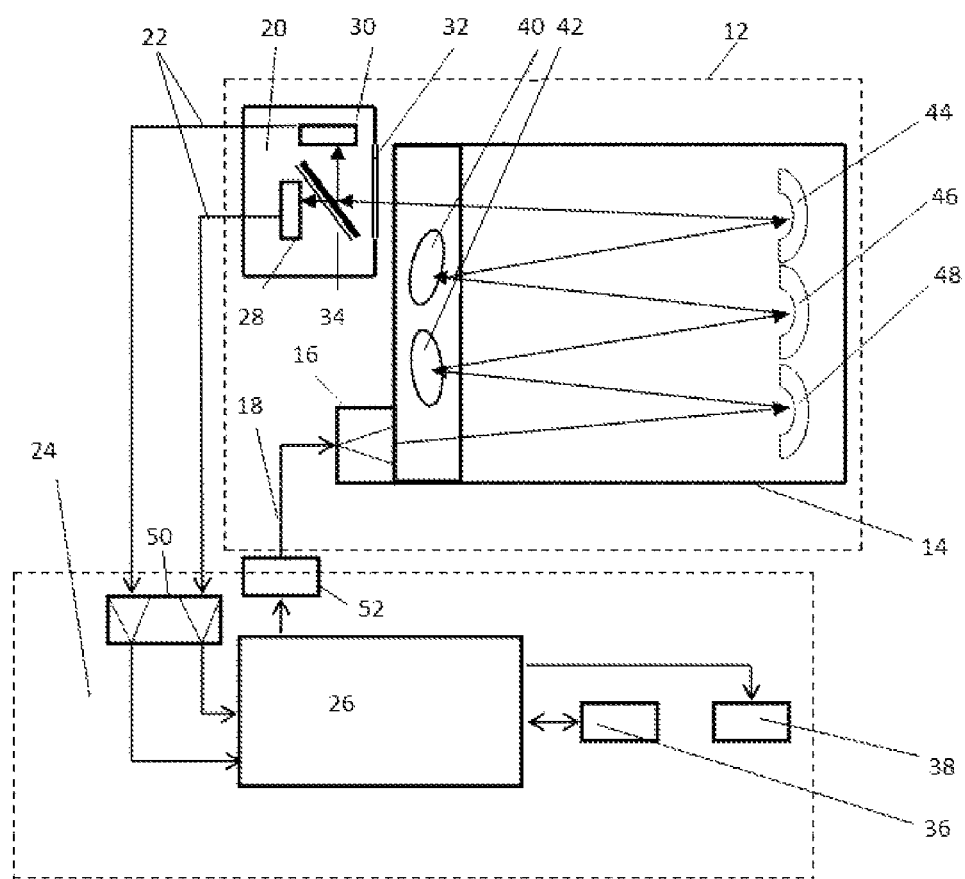
FIG. 1 shows a block diagram of the optical gas analyzer according to the disclosure.

The feasibility of the optical gas analyzer is explained in the following description. The present optical gas analyzer 10 (FIG. 1) comprises an optical unit 12 with an optical gas cell 14 providing for the infrared radiation passage, an infrared radiation source 16 located at the inlet 18 of the optical unit 12, immediately before the gas cell 14, and also a detector 20 of the infrared radiation located at the outlet 22 of the optical unit 12, immediately after of the above-mentioned cell 14. There is also a control unit 24 comprising a microcontroller 26, coupled with the infrared radiation source 16 and the infrared radiation detector 20. The control unit 24 is adapted to change operation modes of the infrared radiation source 16, and to process the infrared radiation, received by the detector 20, to display the results obtained. The optical gas cell 14 is adapted to transmit radiation energy along the zigzag-like trajectory with multiple radiation concentration from its inlet, on a way through it, and at the outlet from it, at the infrared radiation detector 20.

Figure 3:
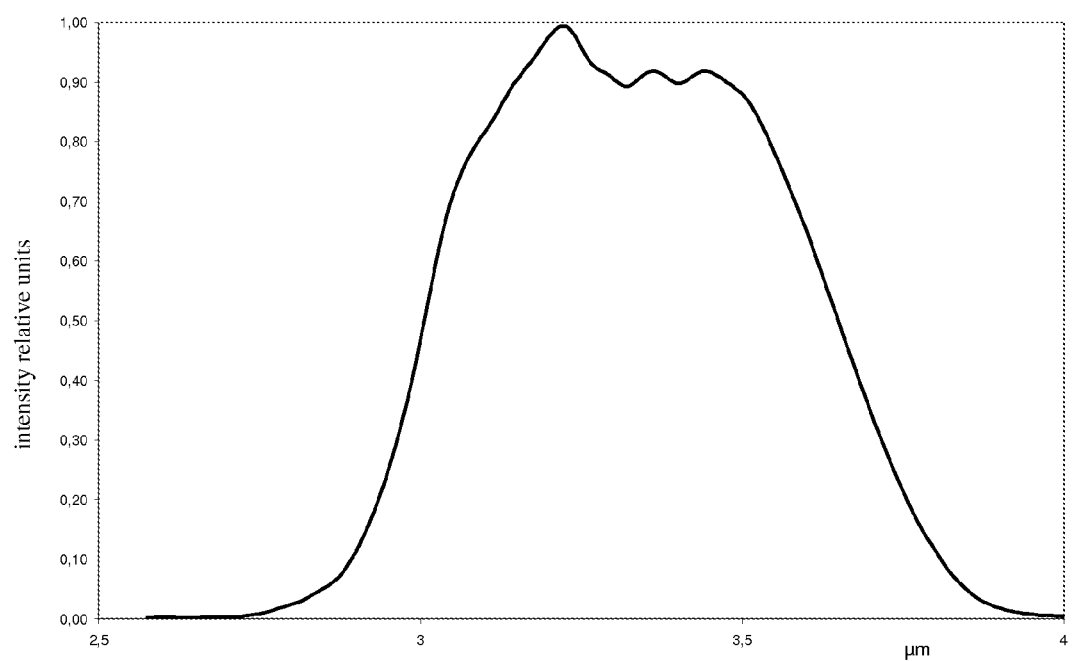
FIG. 3 illustrates a radiation spectrum of the radiation source.
Figure 5:
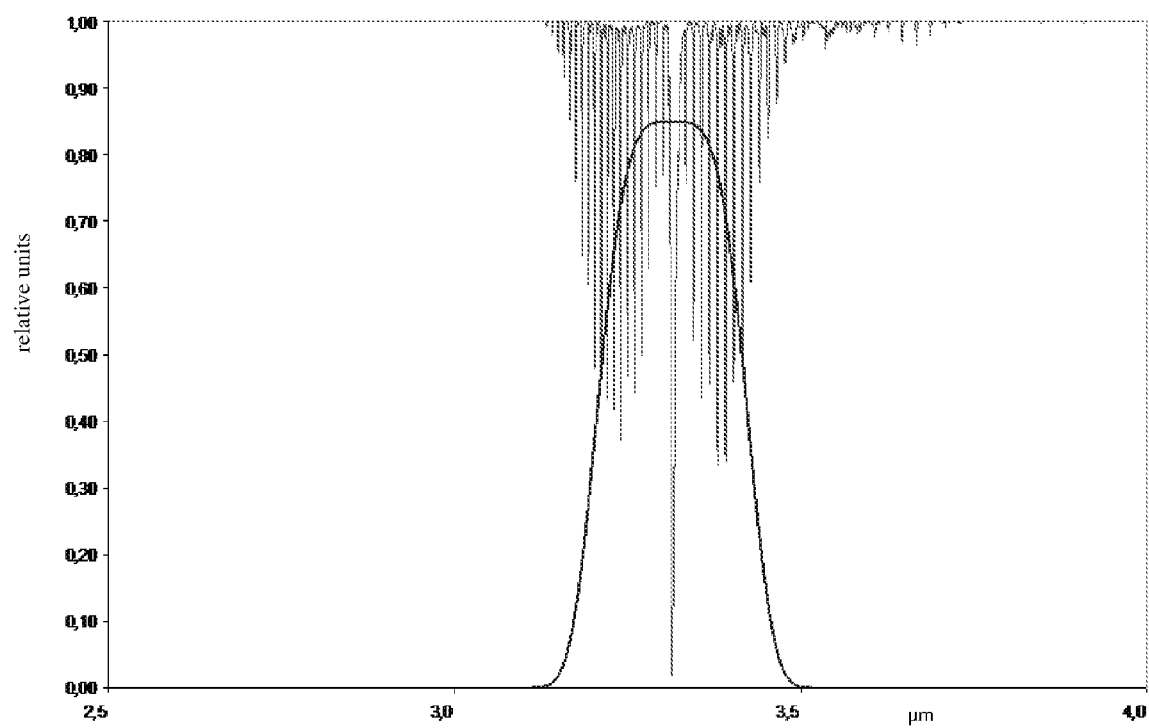
FIG. 5 represents a transmission spectrum of the filter mirror.

The infrared radiation detector 20 includes a differential receiving device comprising a measuring photovoltaic detector 28 and a reference photovoltaic detector 30 located at 90° to each other, as well as a filter window 32 and an interferential filter mirror 34 which are adapted to compensate the external influence exposure exerted upon the infrared radiation trajectory within the above-mentioned cell 14, on the result of measuring the gas concentration. The resulting spectral transmission (FIG. 5) and reflection (FIG. 6) characteristics match the absorption spectrum for the gas to be measured, and the radiation spectrum of the infrared radiation source 16 (FIG. 3), respectively. The above-mentioned compensation of the changes of the trajectory of the radiation passing through the multi-path cell 14 implies that a parasitic influence of that exposure is corrected. For the example being discussed, the transmission characteristic can be analytically presented in the shape of a sum of two Gaussians.

Figure 6:
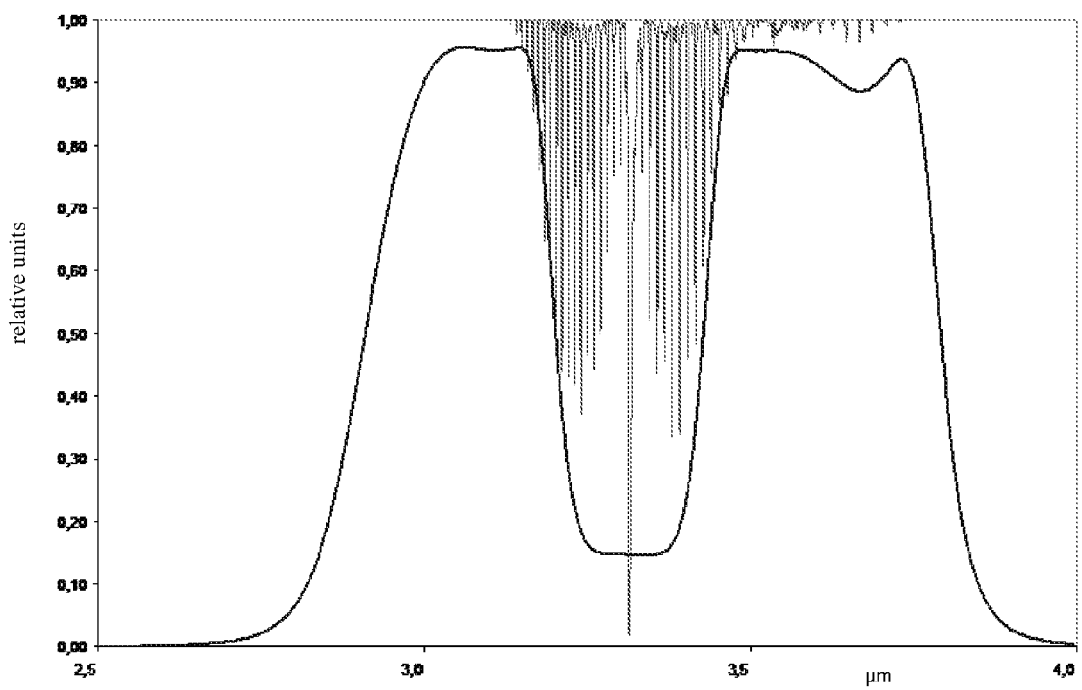
FIG. 6 plots a reflection spectrum of the filter mirror.

The lateral dimension of the caustic at the outlet of the cell 14 for all non-homocentric beams does not exceed the area of the filter window 32 of the IR radiation detector 20. This can be preferably achieved by the proper selection of the mirrors in terms of their diameters and curvature of their surfaces, their mutual arrangement, and angles of their mutual placement. The filter mirror 34 is located between the measuring photovoltaic detector 28 and the reference photovoltaic detector 30, preferably at 45° to normal lines of photo-sensible layers of the detectors. In the direction towards the reference photovoltaic detector 30, the filter mirror 34 possesses a reflection spectrum (FIG. 6). Thus, almost complete usage of light from the infrared radiation source 16 is attained.

The infrared radiation source 16 includes a pulse LED source creating a directed infrared pulse radiation at the inlet of the optical gas cell 14, the switching on/off duty rate of the radiation being coordinated by means of the control unit 24 with the switching on/off duty rate for the above-mentioned receiving device 20.

Used as a microcontroller 26 can be a device within the product range of various manufacturers (i.e. of series MSP430 by Texas Instruments or STM family from the company ST). The control unit 24 also comprises a digital input/output port 36 and an analog output port 38, configured to control the gas analyzer and to transmit the data to a user, for example, security system (not shown at the drawing). The gas analyzer can be placed into a body (not shown at the drawing), the surface of which has openings to allow the gas into the optical cell 14, the openings being adapted to protect against dust through the use of, for example, a dust-protection grid (not shown at the drawing).

Figure 2:
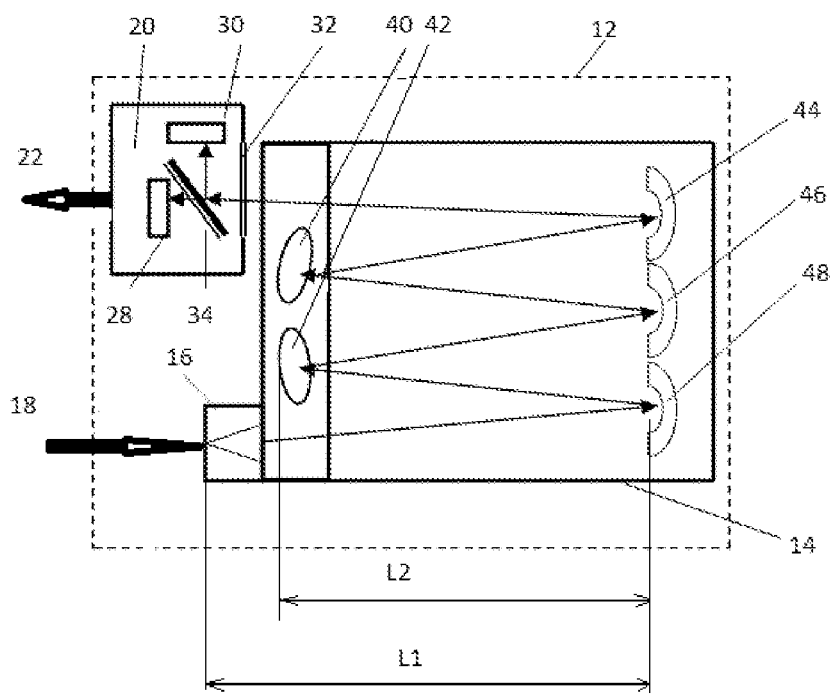
FIG. 2 presents the optical unit of the analyzer in more detail.

The best practical embodiment for the multi-path mirror cell 14 is the one where it is made using flat mirrors and spherical or parabolic mirrors, the number of the latter being larger than the number of the former by one. For example, the cell 14 can comprise two flat mirrors 40 and 42 (FIGS. 1, 2) and three spherical or parabolic surfaces 44, 46, and 48 located, preferably, in check order to form a zigzag-like optical six-path trajectory between them. The number of the mirrors can vary influencing such parameters of the analyzer as its accuracy and dimensions, and, since the cell is a multi-path one, the mirror reflection factor should be high. The infrared radiation source 16 is directed to the first spherical mirror 48 placed at a corresponding angle towards the main optical axis of the cell 14 and adapted to transmit the radiation energy along the zigzag-like trajectory between the mirrors to form an image of the source upon the flat mirrors 40, 42 and on the infrared radiation detector 20. For example, two flat mirrors 40, 42 are located at a certain distance from the spherical mirrors 44, 46, and 48. Particularly (FIG. 2 depicts the distances $L_1$ and $L_2$ by convention), $L_1=2F_1$, where $F_1$ is a focal distance (not shown) of the spherical mirrors 44 and 48. The flat mirrors 40, 42 may be located symmetric to the optical axis of the mirror 46 at the angles providing for the optimal light transmission of the spherical mirror 46 that may have a different focal distance. The spherical mirror 46 is installed, for example, in a manner as to satisfy the formula $L_2=2F_2$, where $F_2$ is a focal distance (not shown) of the spherical mirror 46 and $L_2$ is approximately 10±2 mm. The most preferable is the case where the flat mirrors 40, 42 are symmetrical with regard to the optical axis of the spherical mirror 46.

Applicants have developed and tested an experimental sample of the present gas analyzer shaped in a cylinder of 20 mm in diameter, the height being of 16 mm. The operational principle and the operational results obtained with the analyzer are discussed below. The timing chart of operation for main units of the optical gas analyzer is depictured in FIG. 7.

Figure 7:
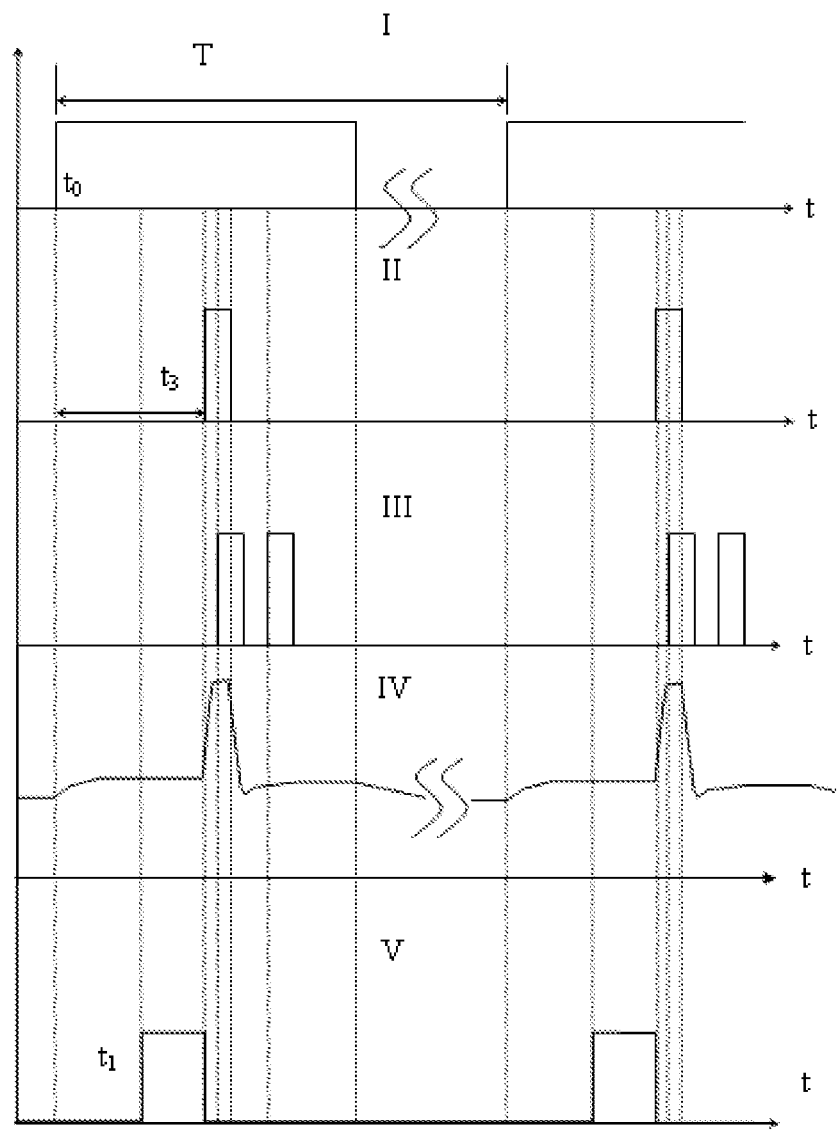
FIG. 7 depicts a timing chart of operation for main units of the optical gas analyzer.

After the gas analyzer power is on and upon completion at the time moment to of the initialization processes of the microcontroller 26, the control unit 24 is switched on to supply power to controlled preliminary amplifiers 50 (diagram I, FIG. 7). After $t_1=75$ μs after the initial time to, the temperature of the optical gas cell 14 is measured for 40 μs (diagram V, FIG. 7). After a delay time t3 from the moment to, the microcontroller 26 starts up a circuit 52 controlling the source 16 of infrared radiation to form a current pulse of 12-15 μs in duration (diagram II, FIG. 7). The source 16 of the infrared radiation forms the infrared radiation beam with a spectrum form shown at FIG. 3. The source 16 of the infrared radiation installed at the inlet of the optical gas cell 14 and connected to the control unit 24, directs the beam to the first spherical mirror 48 located within the gas cell 14.

Figure 4:
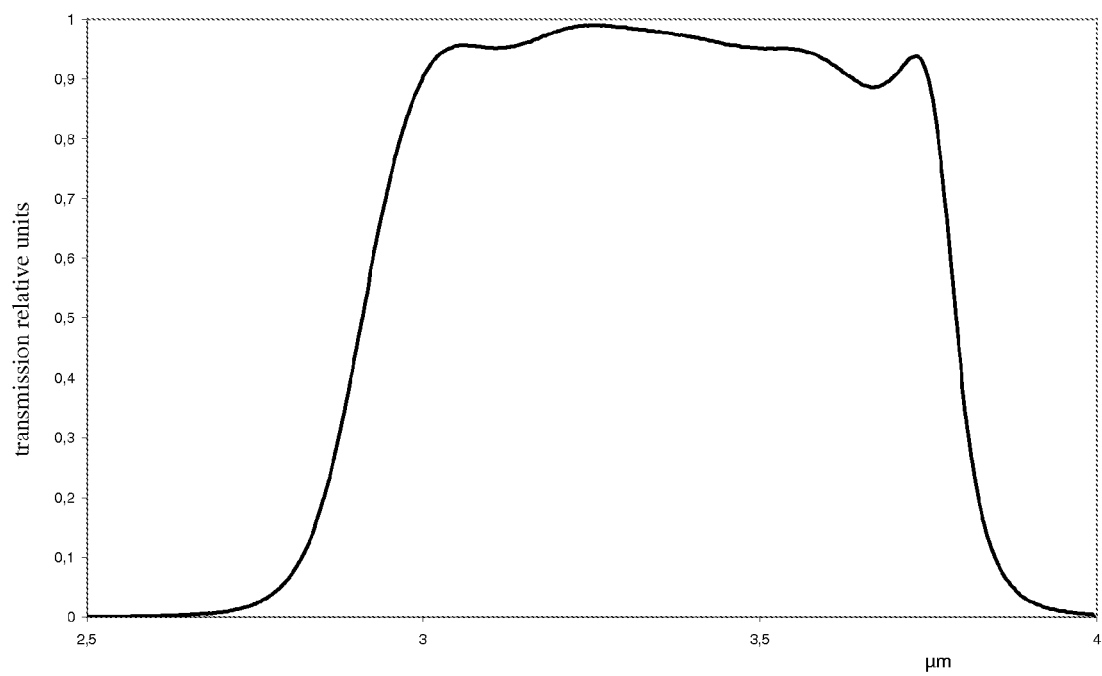
FIG. 4 characterizes a transmission spectrum for the differential photovoltaic detector window.

The gas to be measured, such as methane, incomes from outside environment to the optical gas cell 14 by means of molecular diffusion through respective openings to change the beam spectral characteristic according to its absorption spectrum. Altered by the gas, the beam arrives to the outlet of the cell 14, where the detector 20 of the infrared radiation is installed. The beam passes through the filter window 32, having a transmission spectrum form (FIG. 4) and reaches the interferential filter mirror 34 installed at an angle between the measuring, 28, and the reference, 30, photovoltaic detectors. The filter mirror 34 possesses a form of reciprocal transmission spectrum (FIG. 5) and reflection one (FIG. 6), therefore a portion of the beam from the source 16 of infrared radiation, absorbed by the gas to be analyzed, passes through the filter window 32 of the detector 20 of the infrared radiation with corresponding transmission spectrum form (FIG. 4) to then arrive, through the filter mirror 34, to the measuring fast response photovoltaic detector 28. Whereas another portion of the spectrum of the infrared radiation source 16 is reflected by the filter mirror 34 to the reference fast response photovoltaic detector 30. In this case, the absorption spectra for the measuring and the reference fast response photovoltaic detectors 28, 30 correspond to spectra directed thereto after transmitting and reflecting the beam by the filter mirror 34. Then, in 7.5 μs after starting the current pulse of the source 16 of the infrared radiation, the control unit 24 starts digitizing the signals from the fast response photovoltaic detectors 28 and 30 entering through the preliminary amplifiers 50 the microcontroller 26 of the control unit 24 (diagram III, FIG. 7). In 10 μs after the pulse from the infrared radiation source 16 is cutoff, the control unit 24 digitizes a signal from each of the fast response photovoltaic detectors 28 and 30 at the maximum of those signals (diagram IV, FIG. 7). The signal amplitude for the measuring and the reference fast response photovoltaic detectors 28, 30 is determined as a difference between the digitized values. The microcontroller 26 of the control unit 24 calculates the ratio of amplitudes for the signals of the measuring and the reference fast response photovoltaic detectors 28, 30, makes digital accumulation to improve signal/noise ratio, and calculates the concentration of the gas to be measured. The calculation is based on previously obtained calibration data stored in the microcontroller memory. The temperature correction for the calculated and the accumulated ratios is also carried out based on the calibrated temperature dependence obtained for a given analyzer in the zero concentration of the gas to be measured. The entire measuring period takes about 180 μs, the infrared radiation source 16 being in active mode for 12-15 μs. After this time expires, the control unit 24 goes into a sleep mode to save power, thus completing the measurement cycle. In a predetermined time, for example, 2000 μs from starting $t_0$, the cycle is repeated. In this way, the control unit 24 periodically transmits information about the concentration of the gas to be measured to a user/security system (not shown) via digital and/or analog ports 36, 38. The infrared radiation source 16 pulse power is 300 mW, but, by virtue of the high duty rate, the average power consumption for the source 16 does not exceed 2.5 mW. The overall power consumption by the gas analyzer does not exceed 5 mW. This contributes as well to minimizing the energy consumption. It is noteworthy that the speed-of-response of the detectors implies that the leading-edge pulse time for the case discussed should be units of microseconds. Also, the matching of switching on/off duty rate of the radiation source and switching on/off duty rate for the detectors implies that the moments of the pulses to appear and cease to exist must be in sync with each other. Otherwise, the proper operation of the analyzer cannot be guaranteed.

The above described mode of operation is understood to be a non-limiting, though preferable, example. Moments of turning on/off, durations of pulses and intervals between them can vary depending on the operation mode selected and objects to achieve. Also, concentration of other hydrocarbons can be controlled by the analyzer. They have absorption spectra different from that of methane. The correct selection of the filter mirror spectral characteristic matching the absorption specter of the hydrocarbon of choice will secure the correct result.

With the above in view, a conclusion can be made that the present gas analyzer can be used to measure atmosphere concentration of other hydrocarbons as well, provided a proper calibration of the analyzer has been fulfilled, since it provides for a large path of radiation due to corresponding design location of elements within the cell; uses virtually the entire energy of the infrared radiation source, thus minimizing the losses of energy; secures radiation concentration on the detector thus contributing to enhanced sensitivity (the minimal concentration to be detected is no more than 1% of the Lower Explosive Limit for the above-discussed sample); provides for the required operation mode setup for the control unit, thus minimizing the power consumption; and provides for the compensation of external influences using mechanical stabilization due to designing the differential detector with a built-in filter mirror.

Thus, the present optical gas analyzer offers a fast response and high sensitivity with simultaneous minimization of power consumption and small dimensions as compared with prior art.

What is claimed is:
1. An optical gas analyzer, comprising:
an optical gas cell to pass infrared (IR) radiation therethrough, an IR source, located at the inlet of the optical gas cell,
a detector of the IR radiation, located at the outlet of the cell, and
a control unit, connected to the IR radiation source and the IR radiation detector and adapted to change operation modes of the IR radiation source and to process the IR radiation received by the detector, to display a gas concentration result of the processing,
wherein the optical gas cell is made mirrored and multi-path and adapted to concentrate the IR radiation passing therethrough on the IR radiation detector,
wherein the IR radiation detector comprises a differential receiving device, a filter window, and a filter mirror, the differential receiving device comprising a measuring photovoltaic detector and a reference photovoltaic detector,
the filter window being located at the inlet of the IR radiation detector, the filter mirror, being located inside the IR radiation detector, the filter window and filter mirror being adapted to compensate external influence upon the IR radiation path trajectory within the cell on the gas concentration result, resulting spectral transmission and reflection characteristics of the filter window and filter mirror being correlated with the absorption spectrum for the gas to be measured and with the radiation spectrum of the IR radiation source, respectively, the radiation spectrum of the IR source being in the range between about 2.8 and about 3.8 μm, the transmission spectrum of the filter window being in the range between about 2.8 and about 3.8 μm, the transmission spectrum of the filter mirror being in the range between about 3.1 and about 3.5 μm, and wherein the IR radiation source includes an infrared impulse source of the LED type.

2. The optical gas analyzer of claim 1, wherein the optical gas cell comprises spherical or parabolic mirrors and flat mirrors, the number of the spherical or parabolic mirrors exceeding the number of the flat minors by one, a beam from the infrared radiation source being directed to the first spherical or parabolic mirror, the spherical or parabolic mirrors and the flat mirrors being arranged in a checker order to transmit the beam via a zigzag-like trajectory between the mirrors to create an image of the source upon the flat minors and in the receiving device.

3. The optical gas analyzer of claim 2, wherein the optical gas cell comprises three spherical or parabolic mirrors and two flat mirrors.

4. The optical gas analyzer of claim 1, wherein the measuring and the reference photovoltaic detectors are located perpendicular to each other, and the filter mirror is installed at an angle of about 45° towards normal lines of the measuring and the reference photovoltaic detectors.

5. An optical gas analyzer, comprising:
an optical gas cell to pass infrared radiation (IR) therethrough,
an IR radiation source, located at the inlet of the optical gas cell,
a detector of the IR radiation, located at the outlet of the cell, and
a control unit, connected to the IR radiation source and the IR radiation detector and adapted to change operation modes of the IR radiation source and to process the IR radiation received by the detector, to display a gas concentration result of the processing,
wherein the optical gas cell is made mirrored and multipath and adapted to concentrate the IR radiation passing therethrough on the infrared radiation detector,
wherein the IR radiation detector comprises a differential receiving device, a filter window, and a filter mirror, the differential receiving device comprising a measuring photovoltaic detector and a reference photovoltaic detector, the measuring and the reference photovoltaic detectors being located perpendicular to each other, the filter window being located at the inlet of the IR radiation detector, the filter mirror, being located inside the IR radiation iradiation detector at an angle of about 45° towards normal lines of the measuring and the reference photovoltaic detectors, the filter window and filter mirror being adapted to compensate external influence upon the IR radiation path trajectory within the cell on the gas concentration result, resulting spectral transmission and reflection characteristics of the filter window and filter mirror being correlated with the absorption spectrum for the gas to be measured and with the radiation spectrum of the IR radiation source, respectively, the radiation spectrum of the IR source being in the range between about 2.8 and about 3.8 μm, the transmission spectrum of the filter window being in the range between about 2.8 and about 3.8 μm, the transmission spectrum of the filter mirror being in the range between about 3.1 and about 3.5 μm, and wherein the IR radiation source includes an infrared impulse source of the LED type.

6. The optical gas analyzer of claim 5, wherein the optical gas cell comprises spherical or parabolic mirrors and flat mirrors, the number of the spherical or parabolic mirrors exceeding the number of the flat mirrors by one, a beam from the infrared radiation source being directed to the first spherical or parabolic mirror, the spherical or parabolic mirrors and the flat mirrors being arranged in a checker order to transmit the beam via a zigzag-like trajectory between the mirrors to create an image of the source upon the flat mirrors and in the receiving device.

7. The optical gas analyzer of claim 6, wherein the optical gas cell comprises three spherical or parabolic mirrors and two flat mirrors.

8. A method for measuring concentration of a gas, the method comprising:
generating an IR beam with an IR source,
directing the beam into an optical gas cell,
directing the gas to be measured into the cell to thereby change the transmission spectrum of the beam in accordance with the absorption spectrum of the gas,
directing the beam with the changed transmission spectrum to an IR detector through a filter window and filter mirror,
compensating external influence upon the IR path trajectory within the cell on the result of the measuring,
correlating spectral transmission and reflection characteristics of the filter window and filter mirror with the absorption spectrum of the gas and with the radiation spectrum of the IRR source,
generating a reference signal and a measuring signal in the IRR detector, and
obtaining the required concentration by the ratio of the amplitudes of the reference and measuring signals.

* * * * *